United States Patent [19]
Giret et al.

[11] Patent Number: 5,994,280
[45] Date of Patent: Nov. 30, 1999

[54] CLEANSING COMPOSITIONS COMPRISING AN ANIONIC SURFACTANT AND AMPHOTERIC SURFACTANT MIXTURE

[75] Inventors: Michel Joseph Giret, Sunninghill; Christopher David Leahy, Kew Richmond, both of United Kingdom

[73] Assignee: The Procter & Gamble Company, Cincinnati, Ohio

[21] Appl. No.: 09/079,339

[22] Filed: May 14, 1998

Related U.S. Application Data

[63] Continuation of application No. 08/491,938, Mar. 19, 1996, and a continuation-in-part of application No. 08/847,767, Apr. 22, 1997, which is a continuation of application No. 08/393,141, Feb. 21, 1995, which is a continuation of application No. 08/190,175, Jan. 31, 1994, Pat. No. 5,409,640, which is a continuation of application No. 07/774,684, Oct. 10, 1991, abandoned.

[51] Int. Cl.⁶ .............. C11D 1/94; C11D 3/382; C11D 9/02
[52] U.S. Cl. ............ 510/130; 510/119; 510/121; 510/122; 510/125; 510/129; 510/151; 510/152; 510/153; 510/155; 510/156; 510/159; 510/242; 510/251; 510/337; 510/340; 510/341; 510/353; 510/417; 510/421; 510/426; 510/430; 510/433; 510/434; 510/437; 510/466; 510/477; 510/490; 510/491

[58] Field of Search ................. 510/119, 121, 510/122, 125, 129, 130, 151, 152, 153, 155, 156, 159, 242, 251, 337, 340, 341, 353, 417, 421, 426, 430, 433, 434, 437, 466, 477, 490, 491

[56] References Cited

U.S. PATENT DOCUMENTS

| | | | |
|---|---|---|---|
| 4,346,079 | 8/1982 | Roehl | 424/65 |
| 4,973,422 | 11/1990 | Schmidt | 252/174.11 |
| 4,976,953 | 12/1990 | Orr et al. | 424/47 |
| 5,174,927 | 12/1992 | Honsa | 252/543 |

*Primary Examiner*—Yogendra Gupta
*Assistant Examiner*—Charles Boyer
*Attorney, Agent, or Firm*—Darryl C. Little

[57] ABSTRACT

Cleansing and moisturizing personal cleansing compositions which contain from about 5% to about 50% of a surfactant; from about 3% to about 40% of an insoluble, nonionic oil or wax or mixture thereof; from about 0.1% to about 8% by weight of a fatty acid having an average chain length of from about 10 to about 18 carbon atoms; from about 1.5% to about 10% by weight of citric acid or water soluble citrate salt or mixture thereof; and water are disclosed.

21 Claims, No Drawings

CLEANSING COMPOSITIONS COMPRISING AN ANIONIC SURFACTANT AND AMPHOTERIC SURFACTANT MIXTURE

This application is a continuation of application Ser. No. 08/491,938, filed Mar. 19, 1996. and is a continuation-in-part of application Ser. No. 08/847,767, filed Apr. 22, 1997, which is a continuation of application Ser. No. 08/393,141, filed Feb. 21, 1995, which is a continuation of application Ser. No. 08/190,715, filed Jan. 31, 1994 (U.S. Pat. No. 5,409,640, issued Apr. 25, 1995), which is a continuation of application Ser. No. 07/774,684, filed Oct. 10, 1991 (now abandoned).

The present invention relates to cleansing compositions. In particular it relates to foam-producing personal cleansing compositions suitable for simultaneously cleansing and conditioning the skin and/or the hair and which may be used, for example, in the form of foam bath preparations, shower products, skin cleansers, hand, face and body cleansers, shampoos, etc.

BACKGROUND OF THE INVENTION

Foaming cosmetic compositions must satisfy a number of criteria including cleansing power, foaming properties, mildness/low irritancy and physical stability. Oil-in-water emulsion systems typical of foaming cosmetic compositions represent a particular challenge with respect to stability and viscosity. While on one hand it is possible to ultilise agents specifically to induce appropriate viscosity, care must be taken to ensure these agents work to maintain that viscosity over time. Certain fatty acids are known to be effective in the achievement of matrix viscosity. However this is generally dependant upon the fatty acid forming stable complexes. It has been a particular problem that fatty acid added to achieve stability/viscosity in an oil-in-water emulsion can result in a reduction in viscosity over time. This is believed in part to be due to the secondary formation of insoluble crystalline moieties which break down the structure of the emulsion and lead to lower viscosity/thinning. The aforementioned problems can be exaggerated when products are exposed to extremes or variations of temperature.

Skin is made up of several layers of cells which coat and protect the keratin and collagen fibrous proteins that form the skeleton of its structure. The outermost of these layers, referred to as the stratum corneum, is known to be composed of 250Å protein bundles surrounded by 80Å thick layers. Hair similarly has a protective outer coating enclosing the hair fibre which is called the cuticle. Anionic surfactants can penetrate the stratum corneum membrane and the cuticle and, by delipidization destroy membrane integrity. This interference with skin and hair protective membranes can lead to a rough skin feel and eye irritation and may eventually permit the surfactant to interact with the keratin and hair proteins creating irritation and loss of barrier and water retention functions.

Ideal cosmetic cleansers should cleanse the skin or hair gently, without defatting and/or drying the hair and skin and without irritating the ocular mucosae or leaving skin taut after frequent use. Most lathering soaps, shower and bath products, shampoos and bars fail in this respect.

Certain synthetic surfactants are known to be mild. However, a major drawback of most mild synthetic surfactant systems when formulated for shampooing or personal cleansing is poor lather performance compared to the highest shampoo and bar soap standards. Thus, surfactants that are among the mildest, such as sodium lauryl glyceryl ether sulfonate, (AGS), are marginal in lather. The use of known high sudsing anionic surfactants with lather boosters, on the other hand, can yield acceptable lather volume and quality but at the expense of clinical skin mildness. These two facts make the surfactant selection, the lather and mildness benefit formulation process a delicate balancing act.

Despite the many years of research that have been expended by the toiletries industry on personal cleansing, the broad mass of consumers remain dissatisfied by the mildness of present day cleansing compositions, finding, for example, that they have to apply a separate cosmetic lotion or cream moisturizer to the skin after using a shower or bath preparation in order to maintain skin suppleness and hydration and to counteract the delipidizing effect of the cleanser.

Thus a need exists for personal cleansing products which produce a foam which is abundant, stable and of high quality, which are effective hair and skin cleansers, which will not dehydrate the skin or result in loss of skin suppleness, and which will provide a level of skin conditioning performance in a wash and rinse-off product which previously has only been provided by a separate post-cleansing cosmetic moisturizer, which has good rinsibility characteristics, and which at the same time has stable product and viscosity characteristics and remains fully stable under long term and stressed temperature storage conditions.

SUMMARY OF THE INVENTION

The subject of the present invention is a stable, foaming cleansing product suitable for personal cleansing of the skin or hair and which may be used as foam bath and shower products, skin cleansers and shampoos etc. According to one aspect of the invention, there is provided a personal cleansing composition comprising:

(a) from about 5% to about 50% by weight of one or more surfactants selected from anionic, nonionic, amphoteric, zwitterionic and cationic surfactants and mixtures thereof;

(b) from about 3% to about 40% by weight of an insoluble, nonionic oil or wax or mixture of insoluble, nonionic oils or waxes;

(c) from about 0.1% to about 8% by weight of fatty acid having a weight-average chain length of from-about 10 to about 18 carbon atoms;

(d) from about 1.5% to about 10% by weight of citric acid or water soluble citrate salt or mixture thereof; and (e) water.

In preferred embodiments of the invention comprising mixtures of anionic and amphoteric surfactants, the anionic surfactant and amphoteric surfactant together comprise from about 5% to about 30% by weight of the composition, and the weight ratio of anionic surfactant:amphoteric surfactant is in the range from about 1:5 to about 20:1. Preferably the weight ratio of total surfactant: nonionic oil or wax is in the range from about 10:1 to about 1:3. Preferably also the composition is in the form of an oil-in-water emulsion having a viscosity (Brookfield RVT, Helipath, Spindle TB, 5 rmp, 25° C., 1 min) in the range from 10,000 to 40,000 cps and a yield point of at least 50 dynes/cm$^2$ (Brookfield RVT, Spindle CP52, Plate Code A, 25° C).

All concentrations and ratios herein are by weight of the cleansing composition, unless otherwise specified. Surfactant chain lengths are also on a weight average chain length basis, unless otherwise specified.

The invention relates to a foam-producing cleansing composition with superior physical and viscosity stability characteristics (across temperature conditions) combined with excellent lathering, mildness to the skin and hair, together with good cleansing ability and conditioning performance. The invention also relates to a wash and rinse-off personal cleansing product having the above stability, lathering, mildness, rinsibility and conditioning benefits.

The cleansing compositions herein are based on a combination of mild surfactants which in general terms can be selected from anionic, amphoteric, nonionic and betaine surfactants and mixtures thereof. The compositions preferably comprise a mixture of anionic, nonionic and amphoteric surfactants and highly preferred systems also incorporate a betaine surfactant. Other suitable compositions within the scope of the invention comprise mixtures of anionic with one or more nonionic or betaine surfactants or mixture thereof; and mixtures of amphoteric with one or more nonionic or betaine surfactants or mixture thereof. The level of each of the anionic and amphoteric surfactants is generally in the range from about 1% to about 20%, preferably from about 1% to about 15%, and especially from about 2% to about 13% by weight of the composition. The weight ratio of anionic surfactant:amphoteric surfactant, on the other hand is generally from about 1:5 to about 20:1, preferably from about 1:2 to about 5:1, and especially from about 1:1 to about 2:1. The total level of anionic and amphoteric surfactants is generally about 5% to about 30%, preferably from about 8% to about 25% and especially from about 10% to about 20% by weight of the cleansing composition. The nonionic or betaine surfactant, on the other hand, preferably constitutes from about 0.1% to about 20%, more preferably from about 0.1% to about 10% and especially from about 1% to about 8% by weight of the composition The total level of anionic, nonionic and amphoteric surfactants is generally from about 5% to about 45%, more preferably from about 7% to about 40% by weight of the cleansing composition. The total level of surfactant, inclusive of anionic, amphoteric, nonionic, betaine and other surfactant components, is preferably from about 5% to about 50%, more preferably from about 10% to about 35% by weight of composition.

Anionic surfactants suitable for inclusion in the compositions of the invention can generally be described as mild synthetic detergent surfactants and include ethoxylated alkyl sulfates, alkyl glyceryl ether sulfonates, methyl acyl taurates, fatty acyl glycinates, N-acyl glutamates, acyl isethionates, alkyl sulfosuccinates, alpha-sulfonated fatty acids, their salts and/or their esters, alkyl ethoxy carboxylates, alkyl phosphate esters, ethoxylated alkyl phosphate esters, acyl sarcosinates and fatty acid/protein condensates, and mixtures thereof. Alkyl and/or acyl chain lengths for these surfactants are $C_8$–$C_{22}$, preferably $C_{10}$–$C_{18}$.

Preferred for use herein from the viewpoint of optimum mildness and lathering characteristics are the salts of sulfuric acid esters of the reaction product of 1 mole of a higher fatty alcohol and from about 1 to about 12 moles of ethylene oxide, with sodium and magnesium being the preferred counterions. Particularly preferred are the alkyl sulfats containing from about 2 to 6, preferably 2 to 4 moles of ethylene oxide, such as sodium laureth-2 sulfate and sodium laureth-3 sulfate. In preferred embodiments, the anionic surfactant contains at least about 50%, especially at least about 75% by weight of ethoxylated alkyl sulfate.

Preferred compositions for use herein also contain an amphoteric surfactant. Amphoteric surfactants suitable for use in the compositions of the invention include:

(a) imidazolinium surfactants of formula (I)

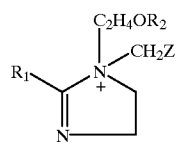

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (II)

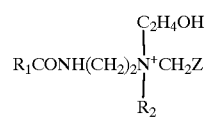

wherein $R_1$, $R_2$ and Z are as defined above;

(b) aminoalkanoates of formula (III)

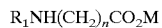

and iminodialkanoates of formula (IV)

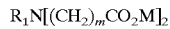

wherein n and m are numbers from b 1to 4, and $R_1$ and M are independently selected from the groups specified above; and (c) mixtures thereof.

Suitable amphoteric surfactants of type (a) are marketed under the trade name Miranol and Empigen and are understood to comprise a complex mixture of species. Traditionally, the Miranols have been described as having the general formula I, although the CTFA Cosmetic Igredient Dictionary, 4th Edition indicates the non-cyclic structure II. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula I and/or II in which $R_1$ is $C_8H_{17}$ (especially isocapryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials preferred for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Empigen CDL60 and CDR 60 (Albright & Wilson), Miranol H2M Conc., Miranol C2M Conc. N.P., Miranol C2M Conc. O.P., Miranol C2M SF, Miranol CM Special (Rhone-Poulenc); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals).

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8$–$C_{18}$ alcohol, $C_8$–$C_{18}$ ethoxylated alcohol or $C_8$–$C_{18}$ acyl glyceride types. Preferred from the viewpoint of mildness and product stability, however, are compositions which are essentially free of (non-ethoxylated) sulfated alcohol surfactants. Note also that the concentrations and weight ratios of the amphoteric surfactants are based herein on the uncomplexed forms of the surfactants, any anionic surfactant counterions being considered as part of the overall anionic surfactant component content.

Examples of suitable amphoteric surfactants of type (b) include salts, especially the triethanolammonium salts and salts of N-lauryl-beta-amino propionic acid and N-lauryl-imino-dipropionic acid. Such materials are sold under the trade name Deriphat by Henkel and Mirataine by Rhone-Poulenc. Amphoterics preferred for use herein, however, are those of formula I and/or II.

The compositions of the invention also contain from about 3% to about 40%, preferably from about 4% to about 20%, and more preferably from about 5% to about 15% by weight of an insoluble nonionic oil or wax or mixture thereof, the oil or wax being insoluble in the sense that it is insoluble in the cleansing composition liquid matrix at a temperature of 25° C. In addition, the oil or wax is present in composition in a level such that the weight ratio of total surfactant:oil or wax is in the range from about 10:1 to about 1:3, preferably from about 5:1 to about 1:2, and especially from about 2:1 to about 1:1, this being preferred from the viewpoint of providing personal cleansing compositions having optimum lathering, mildness, emolliency and rinsibility.

Suitable oils and waxes for use herein can be selected from water-insoluble silicones inclusive of non-volatile polyalkyl and polyaryl siloxane gums and fluids, volatile cyclic and linear polyalkylsiloxnes, polyalkoxylated silicones, amino and quaternary ammonium modified silicones, rigid cross-linked and reinforced silicones and mixtures thereof, $C_1$–$C_{24}$ esters of $C_8$–$C_{30}$ fatty acids such as isopropyl myristate and cetyl ricinoleate, beeswax, saturated and unsaturated fatty alcohols such as behenyl alcohol, hydrocarbons such as mineral oils, petrolatum and squalene, fatty sorbitan esters (see US-A-3988255, Seiden, issued Oct. 26th 1976), lanolin and oil-like lanolin derivatives, animal and vegetable triglycerides such as almond oil, peanut oil, wheat germ oil, linseed oil, jojoba oil, oil of apricot pits, walnuts, palm nuts, pistachio nuts, sesame seeds, rapeseed, cade oil, corn oil, peach pit oil, poppyseed oil, pine oil, castor oil, soybean oil, avocado oil, safflower oil, coconut oil, hazlenut oil, olive oil, grapeseed oil, and sunflower seed oil, and $C_1$–$C_{24}$ esters of dimer and trimer acids such as diisopropyl dimerate, diisostearylmalate, diisostearyldimerate and triisostearyltrimerate. Of the above, highly preferred from the viewpoint of optimum lathering and mildness are the vegetable triglyceride oils.

Preferred from the viewpoint of conditioning effectiveness in a rinse-off application are compositions in the form of oil-in-water emulsions wherein the average size of the emulsion droplets is in the range from about 1 to about 150 microns, preferably from about 2 to about 50 microns. (Droplet size being measured by, for example, laser diffraction using, e.g. a Malvern Series 2600.)

The oil or wax is preferably used herein in combination with a mild surfactant system. Suitable mild surfactants include those having a Relative Skin Barrier Penetration Value of less than about 75, preferably less than about 50 and more preferably less than about 40, Relative Skin Barrier Penetration Value being measured according to the test method set out in EP-A-0203750 (Incorporated herein by reference). Surfactants which have Relative Barrier Penetration Values of greater than 75 can be used along with the mild surfactant at low levels in the compositions of this invention, as long as their use does not significantly change the clinical skin mildness of the total cleansing composition.

Thus according to another aspect of the invention, there is provided a personal cleansing composition comprising:
(a) from about 5% to about 50% by weight of a mixed surfactant system having a Relative Skin Barrier Penetration Value of less than about 75;
(b) from about 3% to about 40% by weight of an insoluble, nonionic oil or wax or mixture of insoluble, nonionic oils or waxes;
(c) from about 0.1% to about 8% by weight of fatty acid having a weight-average chain length of from 10 to 18 carbon atoms;
(d) from about 1.5% to about 10% by weight of citric acid or water soluble citrate salt or mixture thereof; and
(e) water,
wherein the weight ratio of total surfactant: nonionic oil or wax is in the range from about 10:1 to about 1:3, and wherein the composition is in the form of an oil-in-water emulsion having a viscosity (Brookfield RVT, Helipath, Spindle TB, 5 rmp, 25° C., 1 min) in the range from 10,000 to 40,000 cps and a yield point of at least 50 dynes/cm$^2$ (Brookfield RVT, Spindle CPS2, Plate Code A, 25° C).

The compositions herein preferably also contain from about 0.1% to about 20%, more preferably from about 0.1% to about 10%, and C. especially from about 1% to about 8% of a nonionic surfactant. Preferred herein from the viewpoint of optimum lathering and mildness are nonionic surfactants selected from $C_{12}$–$C_{14}$ fatty acid mono- and diethanolamides; polyhydroxy fatty acid amide surfactants having the general formula (VI)

where $R_9$ is H, $C_1$–$C_4$ hydrocarbyl, 2-hydroxyethyl, 2-hydroxypropyl or a mixture thereof, $R_8$ is $C_5$–$C_{31}$ hydrocarbyl and $Z_2$ is a polyhydroxyhydrocarbyl having a linear chain with at least 3 hydroxyls directly connected to said chain, or an alkoxylated derivative thereof; and polyethyleneglycol glyceryl fatty ester surfactants having the formula (VII)

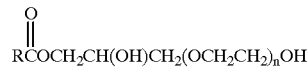

wherein n is from about 5 to about 200, preferably from about 20 to about 100, more preferably from about 30 to about 85, and wherein R comprises an aliphatic radical having from about 5 to 19 carbon atoms, preferably from about 9 to 17 carbon atoms, more preferably from about 11 to 17 carbon atoms, most preferably from about 11 to 14 carbon atoms; and mixtures of said ethanolamide, alkyl polyhydroxy fatty acid amide and/or glyceryl fatty ester surfactants. Also highly preferred herein are compositions which are essentially free of alkyl polysaccharide surfactants, this being preferred from the viewpoint of mildness and processability.

The preferred polyhydroxy fatty acid amide surfactants are those in which $R_9$ is $C_{1-4}$ alkyl, preferably methyl, and $R_8$ is $C_7$–$C_{19}$ alkyl or alkenyl, more preferably straight-chain $C_9$–$C_{17}$ alkyl or alkenyl, or mixture thereof; and $Z_2$ is a polyhydroxyhydrocarbyl having a linear hydrocarbyl chain with at least 3 hydroxyls directly connected to the chain, or an alkoxylated derivative (preferably ethoxylated or propoxylated) thereof. $Z_2$ preferably will be derived from a reducing sugar in a reductive amination reaction; more preferably $Z_2$ is a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2(CHOH)_n$— $CH_2OH$, —$CH(CH_2OH)$—$(CHOH)_n$—1—$CH_2OH$, —$CH_2$ $(CHOH)_2(CHOR')(CHOH)$—$CH_2OH$, where n is an integer from 3 to 5, inclusive, and R' is H or a cyclic or aliphatic monosaccharide, and alkoxylated derivatives thereof. Most preferred are glycityls wherein n is 4, particularly —$CH_2$—$(CHOH)_4$—$CH_2OH$.

The most preferred polyhydroxy fatty acid amide has the formula $R_8(CO)N(CH_3)CH_2(CHOH)_4CH_2OH$ wherein $R_8$ is a C11–C17 straight chain alkyl or alkenyl group.

Suitable glyceryl fatty ester surfactants include polyethyleneglycol derivatives of glyceryl cocoate, glyceryl caproate, glyceryl caprylate, glyceryl tallowate, glyceryl palmate, glyceryl stearate, glyceryl laurate, glyceryl oleate, glyceryl ricinoleate, and glyceryl fatty esters derived from triglycerides, such as palm oil, almond oil, and corn oil, preferably glyceryl tallowate and glyceryl cocoate.

Suitable surfactants of this class are commercially available from Sherex Chemical Co. (Dublin, Ohio, USA) under their Varonic LI line of surfactants. These include, for example, Varonic LI 2 (PEG 28 glyceryl tallowate), Varonic LI 420 (PEG 200 glyceryl tallowate), and Varonic LI 63 and 67 (PEG 30 and PEG 80 glyceryl cocoates), and from Croda Inc. (New York, USA) under their Crovol line of materials, such as Crovol A-40 (PEG 20 almond glyceride), Crovol A-70 (PEG 60 almond glyceride), Crovol MA40 (PEG 20 maize glyceride), Crovol M-70 (PEG 60 maize glyceride), Crovol PK40 (PEG 12 palm kernel glyceride), and Croyol PK-70 (PEG 45 palm kernel glyceride). Especially preferred are monotallowate and cocoate fatty ester derivatives of polyethylene glycol, or mixtures thereof, particularly materials such as PEG 82 glyceryl monotallowate and PEG 30 glyceryl cocoate, and mixtures thereof. Also especially preferred herein is PEG (6) capric/caprylic glyceride (Softigen 767).

The compositions herein preferably also contain from about 0.1% to about 20%, more preferably from about 0.1% to about 10%, and especially from about 1% to about 8% of a betaine surfactant. Betaine surfactants suitable for inclusion in the composition of the invention include alkyl betaines of the formula $R_5R_6R_7N+(CH_2)_nM$ (VIII) and amido betaines of the formula (IX)

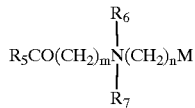

wherein $R_5$ is $C_{12}$–$C_{22}$ alkyl or alkenyl, $R_6$ and $R_7$ are independently $C_1$–$C_3$ alkyl, M is H, alkali metal, alkaline earth metal, ammonium or alkanolammonium, and n, m are each numbers from 1 to 4. Preferred betaines include cocoamidopropyldimethylcarboxymethyl betaine and laurylamidopropyldimethylcarboxymethyl betaine and Tego betaine.

The compositions of the invention also contain from about 0.1% to about 8% preferably from about 0.5% to about 6%, and especially from about 1.5% to about 5% by weight of saturated acyl fatty acids having a weight average chain length of from 10 to 18, preferably from 12 to 16 carbon atoms. Highly preferred is myristic acid. The fatty acid is valuable both from the viewpoint of providing emolliency benefits and also in combination with the citrate for controlling the viscosity of the final composition.

The compositions of the invention preferably also contain a carionic or nonionic polymeric skin or hair conditioning agent at a level from about 0.01% to about 5%, preferably from about 0.04% to about 2% and especially from about 0.05% to about 1% The polymer is found to be valuable for enhancing the creaminess and quality of the foam as well as providing a hair or skin conditioning utility. In addition to the above the polymer is found to be valuable for enhancing the mildness of the product via mitigating the effects of harsher surfactant moieties.

Suitable polymers are high molecular weight materials (mass-average molecular weight determined, for instance, by light scattering, being generally from about 2,000 to about 3,000,000, preferably from about 5,000 to about 1,000,000).

Useful polymers are the cationic, nonionic, amphoteric, and anionic polymers useful in the cosmetic field. Preferred are cationic and nonionic polymers used in the cosmetic fields as hair or skin conditioning agents.

Representative classes of polymers include cationic and nonionic polysaccharides; cationic and nonionic homopolymers and copolymers derived from acrylic and/or methacrylic acid; cationic and nonionic cellulose resins; cationic copolymers of dimethyldiallylammonium chloride and acrylic acid; cationic homopolymers of dimethyldiallylammonium chloride; cationic polyalkylene and ethoxypolyalkylene imines; quaternized silicones, and mixtures thereof.

By way of exemplification, cationic polymers suitable for use herein include cationic guar gums such as hydroxypropyl trimethyl ammonium guar gum (d.s. of from 0.11 to 0.22) available commercially under the trade names Jaguar C-14-S(RTM) and Jaguar C-17(RTM) and also Jaguar C-16 (RTM), which contains hydroxypropyl substituents (d.s. of from 0.8–11) in addition to the above-specified cationic groups, and quaternized cellulose ethers available commercially under the trade names Ucare Polymer JR and Celquat. Other suitable cationic polymers are homopolymers of dimethyldiallylammonium chloride available commercially under the trade name Merquat 100, copolymers of dimethyl aminoethylmethacrylate and acrylamide, copolymers of dimethyldiallylammonium chloride and acrylamide, available commercially under the trade names Merquat 550 and Merquat S, quaternized vinyl pyrrolidone acrylate or methacrylate copolymers of amino alcohol available commercially under the trade name Gafquat, and polyalkyleneimines such as polyethylenimine and ethoxylated polyethylenimine.

The viscosity of the final composition (Brookfield RVT, Helipath, Spindle T-B, 5 rpm, 25° C., 1 min) is preferably in the range of from about 10,000 to about 40,000 cps, more preferably from about 20,000 to about 30,000 cps and a yield point (shear stress at zero shear rate) of at least 50 dynes/cm², preferably at least 100 dynes/cm² (Brookfield RVT, Spindle CP52, Plate Code A, 25° C.). Preferred compositions have non-Newtonian viscosity characteristics. In highly preferred embodiments, the composition of the invention also display a shear stress versus temperature profile such that $(S_{45}-S_5)/S_5$ is less than about 0.4, preferably less than about 0.2, and more preferably less than about 0.1, where $S_t$ is the shear stress in dynes/cm$^2$ at temperature t(° C.) and at a shear rate of 500 sec$^{-1}$ (Brookfield RVT, Spindle CP52, Plate Code A).

Another essential component of the compositions of the invention is citric acid or water soluble citrate salt or mixtures thereof, especially Na, K, NH$_4$ salts, at a level from about 1.5% to about 10% by weight preferably from about 2% to about 8% by weight, most preferably from about 2.5% to about 6% by weight. Citrate is important for providing improved physical and viscosity characteristics in combination with the oil and fatty acid components.

It is a feature of the compositions of the invention that the particular combination of ingredients employed therein give excellent stability even in the presence of fatty acids which can display crystallisation characteristics. Furthermore it is noted that this excellent stability is observed even in the absence of known stabilising agents/viscosity modifiers.

The cleansing compositions can optionally include a hair or skin moisturizer which is soluble in the cleansing composition matrix. The preferred level of moisturizer is from about 0.5% to about 20% by weight. In preferred embodiments, the moisturizer is selected from:

1. water-soluble liquid polyols;
2. essential amino acid compounds found naturally occurring in the stratum corneum of the skin; and
3. water-soluble nonpolyol nonocclusives and mixtures thereof.

Some examples of more preferred nonocclusive moisturizers are glycerine, polyethylene glycol, propylene glycol, sorbitol, polyethylene glycol and propylene glycol ethers of methyl glucose (e.g. methyl glucam-20), polyethylene glycol and propylene glycol ethers of lanolin alcohol (e.g. Solulan-75), sodium pyrrolidone carboxylic acid, lactic acid, urea, L-proline, guanidine, pyrrolidone, hydrolyzed protein and other collagenderived proteins, aloe vera gel and acetamide MEA and mixtures thereof. Of the above, glycerine is highly preferred.

An additional optional component of the composition of the invention is an adduct prepared from vegetable oils containing non-conjugated polyunsaturated fatty acid esters which are conjugated and elaidinized and then modified via Diels-Alder addition with a member of the goup consisting of acrylic acid, fumaric acid and maleic anhydride. The vegetable oil adduct preferably has the general formula (X).

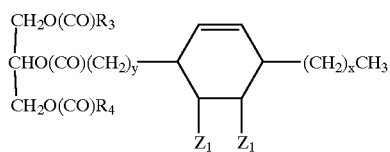

wherein x, y are integers of from 3 to 9, R$_3$ and R$_4$ are independantly selected from saturated and unsaturated C$_7$–C$_{22}$ hydrocarbyl, each Z being CO$_2$M and wherein M is H, or a salt forming cation, preferably alkalimetal, ammonium or alkanol ammonium. The adducts and their preparation are described in U.S. Pat. No. -4,740,367, the adducts being marketed under the trade name Ceraphyl GA (Van Dyke). The vegetable oil adduct is preferably added from about 0.5% to about 5%, preferably from about 1% to about 4% by weight of the composition, A number of further additional optional materials can be added to the cleansing compositions. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, Bronopol (2-bromo-2-nitropropane-1,3-diol), sodium benzoate and 2-phenoxyethanol; other moisturizing agents such as hyaluronic acid, chitin , and starch-grafted sodium polyacrylates such as Sanwet (RTM)IM-1000, IM-1500 and IM-2500 available from Celanese Superabsorbent Materials, Portsmith, Va., USA and described in U.S. Pat. No. -4,076,663; solvents such as hexylene glycol and propylene glycol; anti-bacterial agents such as Oxeco (phenoxy isopropanol); low temperature phase modifiers such as ammonium ion sources (e.g. NH$_4$ Cl); viscosity control agents such as magnesium sulfate and other electrolytes; colouring agents; pearlescers and opacifiers such as ethylene glycol distearate, TiO$_2$ and TiO$_2$-coated mica; perfumes and perfume solubilizers etc; zeolites such as Valfor BV400 and derivatives thereof; and Ca$^{2+}$/Mg$^{2+}$sequestrants such as polycarboxylates, aminopolycarboxylate, polyphosphates, polyphosphonates, aminopolyphosphonates and gluconates etc. Water is also present at a level preferably of from about 45% to about 92% preferably at least about 60% by weight of the compositions herein.

The pH of the compositions is preferably from about 4 to about 8, more preferably from about 4.5 to about 6.5.

The invention is illustrated by the following non-limiting examples.

In the examples, all concentrations are on a 100% active basis and the abbreviations have the following designation:

| | |
|---|---|
| Amphoteric 1 | Empigen CDL 60-an aqueous mixture of 23.5% cocoamphoacetate (the amphoteric of formula I and/or IV in which R$_1$ is coconut alkyl, R$_2$ is H, and Z is CO$_2$Na) and 1.35% cocoamphodiacetate (the amphoteric of formula I and/or IV in which R$_1$ is coconut alkyl, R$_2$ is CH$_2$CO$_2$Na and Z is CO$_2$Na). |
| Amphoteric 2 | Sodium N-lauryl-beta-amino-propionate. |
| Anionic 1 | Sodium laureth-2 sulfate |
| Anionic 2 | Magnesium sodium laureth 3.6 sulfate |
| GA | Polyhydroxy fatty acid amide of formula VII in which R$_8$ is C$_{11}$–C$_{17}$ alkyl, R$_9$ is methyl, and Z$_2$ is CH$_2$(CHOH)$_4$CH$_2$OH |
| DEA | Coconut diethanolamide |
| MEA | Coconut monoethanolamide |
| Betaine | Cocoamidopropyldimethylcarboxymethyl betaine |
| Polymer 1 | Merquat 550-Copolymer of acrylamide and dimethyldiallyl amonium chloride, m. wt. 2.5 × 10$^6$ (8% solution) |
| Polymer 2 | Polymer JR-400-hydroxyethylcellulose reacted with epichlorohydrin and quaternized with trimethylamine, m. wt. 4 × 10$^6$ |
| MA | Myristic Acid |
| Ceraphyl GA | Maleated Soyabean Oil marketed by Van Dyke |
| Preservative | DMDM Hydantoin |
| Pearlescer | Ethyleneglycoldistearate/emulsifier mixture |
| Oil | Soyabean oil |
| Softigen 767 | PEG(6) caprylic/capryl glycerate |
| Mg | Magnesium sulfate heptahydrate |

EXAMPLES I to VII

The following are personal cleansing compositions in the form of shower foam products and which are representative of the present invention:

| | I | II | III | IV | V | VI | VII |
|---|---|---|---|---|---|---|---|
| Amphoteric 1 | 7.5 | 3.0 | 5.0 | 5.0 | 2.5 | 5.0 | 5.0 |
| Amphoteric 2 | — | 5.0 | 3.0 | — | 5.0 | — | — |
| Anionic 1 | 2.5 | — | 6.0 | 4.0 | 7.5 | 10.0 | 10.0 |
| Anionic 2 | 5.0 | 9.0 | 4.0 | 6.0 | — | — | — |
| GA | — | 1.0 | — | 2.0 | 2.0 | — | 2.5 |
| DEA | 3.0 | 1.0 | — | 2.0 | 1.0 | 3.0 | — |
| MEA | — | — | — | — | — | — | 3.0 |
| Betaine | — | 2.0 | 2.0 | 1.0 | 2.5 | 2.5 | — |
| Polymer 1 | — | 0.1 | 0.2 | — | 0.1 | 0.2 | — |
| Polymer 2 | 0.2 | 0.1 | — | 0.2 | 0.1 | — | 0.2 |
| Softigen 767 | — | — | — | — | — | 2.0 | 1.0 |
| MA | 4.0 | 2.0 | 1.5 | 1.0 | 2.0 | 2.0 | 2.0 |
| Ceraphyl GA | 2.0 | 1.0 | — | — | — | 2.0 | 1.0 |
| Oil | 8.0 | 12.0 | 9.0 | 12.0 | 8.0 | 10.0 | 11.0 |
| Preservative | 0.15 | 0.15 | 0.15 | 0.15 | 0.15 | 0.2 | 0.2 |
| Pearlescer | 0.5 | — | — | 1.0 | 1.0 | 2.0 | 1.0 |
| Perfume | 1.0 | 1.0 | 1.0 | 1.0 | 1.0 | 1.0 | 1.0 |
| Glycerine | — | — | — | — | — | — | 3.0 |
| Mg | 1.0 | — | — | — | 2.0 | — | — |
| Sodium Citrate | 2.0 | 3.0 | 2.0 | 5.0 | 2.0 | 4.0 | 3.0 |
| Water | | | | to 100 | | | |

Compositions I to VII are prepared by forming a surfactant phase A containing a portion of the water, the anionic and amphoteric surfactants and the remaining water-soluble, oil-insoluble ingredients, forming an oil phase B containing the MA, DEA, Softigen and oil, admixing B with A at about 40°–70° C., cooling to ambient temperature, then adding the remaining water, preservative and perfume. The average particle size of the emulsion droplets is about 5 micron. (Malvern Series 2600 laser diffraction). The compositions have a viscosity (Brookfield RVT, Helipath, Spindle TB, 5 rmp, 25° C., 1 min) in the range from 10,000 to 40,000 cps and a yield point of at least 50 dynes/cm$^2$ (Brookfield RVT, Spindle CP52, Plate Code A, 25°).

The cleansing products demonstrate excellent physical stability and viscosity characteristics across temperature in addition to good lathering, rinsibility and conditioning benefits.

We claim:

1. A personal cleansing composition comprising:
   (a) from about 5% to about 50% by weight of a mixture of anionic surfactant and amphoteric surfactant,
   (b) from about 3% to about 40% by weight of an insoluble, nonionic oil or wax or mixture of insoluble nonionic oils or waxes;
   (c) from about 0.1% to about 8% by weight of fatty acid having a weight-average chain length of from about 10 to about 18 carbon atoms;
   (d) from about 1.5% to about 10% by weight of a citric acid or water-soluble citrate salt or mixtures thereof; and
   (e) water.

2. A composition according to claim 1 wherein the composition is in the form of an oil-in-water emulsion having a viscosity (Brookfield RVT, Helipath, Spindle TB, 5 rpm, 25° C., 1 min) in the range of from 10,000 to 40,000 cps and a yield point of at least 50 dynes/cm$^2$ (Brookfield RVT, Spindle CP52, Plate Code A, 25° C.).

3. A composition according to claim 1 wherein citric acid or water soluble salt thereof is present at from about 2% to about 8% by weight.

4. A composition according to claim 1 wherein the anionic surfactant is selected from the group consisting of ethoxylated alkyl sulfates, alkyl glyceryl ether sulfonates, methyl acyl taurates, fatty acyl glycinates, N-acyl glutamates, acyl isethionates, alkyl sulfosuccinates, alpha-sulfonated fatty acids, their salts or their esters, alkyl ethoxy carboxylates, alkyl phosphate esters, ethoxylated alkyl phosphate esters, acyl sarcosinates and fatty acid/protein condensates, and mixtures thereof.

5. A composition according to claim 1 which comprises a mixture of anionic surfactant and amphoteric surfactant each in a level of from about 1% to about 15% by weight.

6. A composition according to claim 4 wherein the anionic surfactant comprises an ethoxylated $C_8$–$C_{22}$ alkyl sulfate.

7. A composition according to claim 1 wherein the amphoteric surfactant is selected from the group consisting of:

(a) imidazolinium derivatives of formula (I)

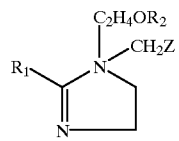

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (II)

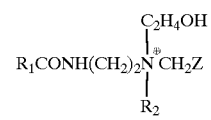

wherein $R_1$, $R_2$ and Z are defined above;
   (b) aminoalkanoates of formula (III)

and iminodialkanoates of formula (IV)

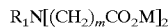

wherein n and m are numbers from 1 to 4, and $R_1$ and M are independently selected from the groups specified in (a) above; and
   (c) mixtures thereof.

8. A composition according to claim 7 wherein the amphoteric surfactant is selected from the group consisting of imidazolinium derivatives of formula (I) or ammonium derivatives of formula (II) or mixtures thereof.

9. A composition according to claim 5 wherein the weight ratio of anionic surfactant to amphoteric surfactant is in the range from about 1:2 to about 5:1.

10. A composition according to claim 9 wherein the weight ratio of anionic surfactant to amphoteric surfactant is in the range from about 1:1 to about 2:1.

11. A composition according to claim 5 wherein the anionic surfactant and amphoteric surfactant is in the range of from about 8% to about 25% by weight of the composition.

12. A composition according to claim 5 additionally comprising from about 0.1% to about 20% by weight of nonionic surfactant.

13. A composition according to claim 12 wherein the nonionic surfactant is selected from $C_{12}$–$C_{14}$ fatty mono-and diethanolamides; polyhydroxy fatty acid amide surfactants having the formula $R_8(CO)N(R_9)Z_2$ wherein $R_9$ is H, $C_1$–$C_4$ hydroxycarbyl, 2-hydroxyethyl, 2-hydroxypropyl, or a mixture thereof, $R_8$ is $C_5$–$C_{31}$ hydroxcarbyl and $Z_2$ is a polyhydroxycarbyl having a linear chain with at least 3 hydroxyls directly connected to said chain, or an alkoxylated derivative thereof, polyethyleneglycol glyceryl fatty ester surfactants having the formula (VII)

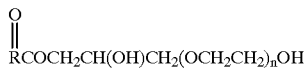

$$RCOCH_2CH(OH)CH_2(OCH_2CH_2)_nOH$$

wherein n is from about 5 to about 200, wherein R comprises an aliphatic radical having from about 5 to 19 carbon atoms; and mixtures of said ethanolamide, polyhydroxy fatty acid amide and glyceryl fatty ester surfactants.

14. A composition according to claim 1 comprising from about 4% to about 20% by weight of nonionic oil or wax or mixture thereof.

15. A composition according to claim 12 wherein the anionic nonionic and amphoteric surfactant together comprise from about 5% to about 45% by weight of the composition.

16. A composition according to claim 1 comprising from about 0.1% to about 20% by weight of betaine surfactant.

17. A composition according to claim 1 comprising from about 0.5% to about 6% by weight of fatty acid having a weight-average chain length of from 12 to 16 carbon atoms.

18. A composition according to claim 1 additionally comprising form 0.01% to 5% of a cationic or nonionic polymeric skin or hair conditioning agent, selected from cationic and nonionic polysaccharides; cationic and nonionic homopolymers and copolymers derived from acrylic or methacrylic acid or mixtures thereof, cationic and nonionic cellulose resins; cationic copolymers of dimethyldiallyammonium chloride and acrylic acid; cationic homopolymers of dimethyldiallyammonium chloride; cationic polyalkylene and ethoxypolyalkylene iminines; quaternized silicones, and mixtures thereof.

19. A composition according to claim 1 additionally comprising a moisturizer selected from the group consisting of glycerin, polyethylene glycol, propylene glycol, sorbitol, polyethylene glycol and polypropylene glycol ethers of methyl glucose, polyethylene glycol and polypropylene glycol ethers of lanolin alcohol, PEG(6) capric/caprylic glyceride, PEG(6) coconut glyceride, sodium pyrrolidone, carboxylic acid, lactic acid, L-proline and mixtures thereof.

20. A composition according to claim 1 wherein the anionic surfactant comprises at least 50% thereof of ethoxylated $C_8$–$C_{22}$ alkyl sulfate.

21. A composition according to claim 1 wherein the weight ratio of total surfactant:nonionic oil or wax is in the range from about 5:1 to about 1:2.

* * * * *